(12) United States Patent
Lee et al.

(10) Patent No.: US 8,890,134 B2
(45) Date of Patent: Nov. 18, 2014

(54) ORGANIC PHOTOELECTRIC MATERIAL AND ORGANIC PHOTOELECTRIC DEVICE AND IMAGE SENSOR

(71) Applicant: Samsung Electronics Co., Ltd., Suwon-Si, Gyeonggi-Do (KR)

(72) Inventors: Kwang Hee Lee, Yongin-si (KR); Kyu Sik Kim, Yongin-si (KR); Kyung Bae Park, Hwaseong-si (KR); Dong-Seok Leem, Hwaseong-si (KR); Seon-Jeong Lim, Yongin-si (KR); Yong Wan Jin, Seoul (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 0 days.

(21) Appl. No.: 13/930,445

(22) Filed: Jun. 28, 2013

(65) Prior Publication Data

US 2014/0008619 A1    Jan. 9, 2014

(30) Foreign Application Priority Data

Jul. 6, 2012    (KR) .................. 10-2012-0073981

(51) Int. Cl.
| | | |
|---|---|---|
| H01L 51/00 | (2006.01) | |
| C07D 495/04 | (2006.01) | |
| H01B 1/12 | (2006.01) | |
| H01L 51/42 | (2006.01) | |

(52) U.S. Cl.
CPC .......... *H01L 51/0071* (2013.01); *C07D 495/04* (2013.01); *H01L 2251/308* (2013.01); *H01L 51/0074* (2013.01); *H01L 51/424* (2013.01); *H01L 51/0094* (2013.01); *H01L 51/0072* (2013.01); *H01B 1/12* (2013.01)
USPC .................... 257/40; 549/41; 549/4; 548/417

(58) Field of Classification Search
USPC ............................ 257/40; 549/41, 4; 548/417
See application file for complete search history.

(56) References Cited

U.S. PATENT DOCUMENTS

| | | |
|---|---|---|
| 2010/0053387 A1 | 3/2010 | Kim et al. |
| 2010/0168444 A1 | 7/2010 | Chen et al. |
| 2010/0305288 A1 | 12/2010 | He et al. |
| 2013/0167930 A1 | 7/2013 | Hildebrandt et al. |
| 2013/0167931 A1 | 7/2013 | Hildebrandt et al. |

FOREIGN PATENT DOCUMENTS

| | | |
|---|---|---|
| CN | 101798310 A | 8/2010 |
| DE | 102009036110 A1 | 12/2010 |
| EP | 1279691 A1 | 1/2003 |
| EP | 2400575 A1 | 12/2011 |
| JP | 2010083785 A | 4/2010 |
| JP | 2010093785 A | 4/2010 |
| JP | 2011029219 A | 2/2011 |
| JP | 2011029220 A | 2/2011 |
| JP | 2012036180 A | 2/2012 |
| KR | 20100136931 A | 12/2010 |
| WO | WO-9912989 A1 | 3/1999 |
| WO | WO-2010020329 A1 | 2/2010 |
| WO | WO-2011/161262 A1 | 12/2011 |
| WO | WO-2011161170 A1 | 12/2011 |
| WO | WO-2011161262 A1 | 12/2011 |

OTHER PUBLICATIONS

Kazuo Takimiya, Thienoacene-based Organic Semiconductors, 2011 Wiley-VCH Verlag GmbH & Co., Advanced Materials, pp. 1-24.

Weimin Zhang, Indacenodithiophene Semiconducting Polymers for High-Performance, Air-Stable Transistors, 2010 American Chemical Society, pp. 11437-11439.

Raja Shahid Ashraf, Silaindacenodithiophene Semiconducting Polymers for Efficient Solar Cells and High-Mobility Ambipolar Transistors, 2010 American Chemical Society, pp. 768-770.

Ted M. Pappenfus, Reduced Band Gap Dithieno[3,2-b:2',3'-d]Pyrroles: New N-Type Organic Materials Via Unexpected Reactivity, Organic Letters 2008, vol. 10, No. 8, pp. 1553-1556.

Yen-Ju Cheng, Carbazole-based Ladder-Type Heptacylic Arene with Aliphatic Side Chains Leading to Enhanced Effiency of Organic Photovoltaics, 2011 American Chemical Society, pp. 2361-2369.

Xugeng Guo, Theoretical Investigations of the Structures and Electronic Spectra of 2-Dicyanovinyldithieno[2,3-b:,3',2'-d]Thiophene (DCST) and 2-Dicyanovinyldithieno[3,2-b:2',3'-d]Thiophene (DCTT), Journal of Molecular Structure: Theochem, 2009, pp. 179-184.

Ravi Kumar Cheedarala, Ladder-Type Heteroacene Polymers Bearing Carbazole and Thiophene Ring Units and Their Use in Field-Effect Transistors and Photovoltaic Cells, Journal of Materials Chemistry, The Royal Society of Chemistry 2011, pp. 843-850.

Ali Yassin, Evaluation of Bis-Dicyanovinyl Short-Chain Conjugated Systems As Donor Materials for Organic Solar Cells, Solar Energy Materials & Solar Cells, 2010 Elsevier B.V., pp. 462-468.

X. Zhang et al. "Effect of Ring Fusion on the Electronic Absorption and Emission Properties of Oligothiophenes"; Journal of Organic Chemistry, vol. 68, pp. 9813-9815, 2003; XP002343472.

Zhang et al. "Synthesis and Structure of Fused α-Oligothiophenes with up to Seven Rings"; Journal of the American Chemical Society, vol. 127, pp. 10502-10503, 2005; XP008139244.

M. Jørgensen et al. "Easy Access to 3,8-Diaryldifurano[2,3-a:2',3'-f]naphthalenes. A New Extended Aromatic System"; Journal of Organic Chemistry, vol. 65, pp. 8783-8785, 2000; XP0055006875.

(Continued)

*Primary Examiner* — Kristin Vajda

(74) *Attorney, Agent, or Firm* — Harness, Dickey & Pierce, P.L.C.

(57) ABSTRACT

An organic photoelectric material may include a compound represented by the above Chemical Formula 1, and an organic photoelectric device and an image sensor including the organic photoelectric material.

18 Claims, 9 Drawing Sheets

(56) References Cited

OTHER PUBLICATIONS

Y. Cheng et al. "Carbazole-Based ladder-Type Heptacylic Arene with Aliphatic Side Chains leading to Enhanced Efficiency of Organic Photovoltaics"; Chemistry of Materials, vol. 23, pp. 2361-2369, 2011; XP0055121925.

C. Tseng et al. "A pentacyclic Nitrogen-Bridged Thienyi-Phenylene-Thienyl Arene for Donor-Acceptor Copolymers: Synthesis, Characterization, and Applications in Field-Effect Transistors and Polymer Solar Cells"; Chemistry—An Asian Journal, vol. 7, pp. 2102-10, 2012; XP0055121926.

Y. Sun et al. "Chemically Doped and Cross-linked Hole-Transporting Materials as an Efficient Anode Buffer layer for Polymer Solar Cells"; Chemistry of Materials, vol. 23, pp. 5006-5015, 2011; XP0055121934.

K. Xiao et al. "A highly p-stacked organic semiconductor for field-effect transistors based on linearly condensed pentathienoacene"; Journal of the American Chemical Society, vol. 127, pp. 13281-13286, 2005; XP55122393.

European Search Report dated Jun. 18, 2014 for corresponding application No. 13 175 391.5.

ORGANIC PHOTOELECTRIC MATERIAL AND ORGANIC PHOTOELECTRIC DEVICE AND IMAGE SENSOR

CROSS-REFERENCE TO RELATED APPLICATION

This application claims priority to and the benefit of Korean Patent Application No. 10-2012-0073981 filed in the Korean Intellectual Property Office on Jul. 6, 2012, the entire contents of which are incorporated herein by reference.

BACKGROUND

1. Field

Example embodiments relate to an organic photoelectric material, and an organic photoelectric device and an image sensor including the organic photoelectric material.

2. Description of the Related Art

A photoelectric device refers to a device for converting light into an electrical signal using photoelectric effects. The photoelectric device may include a photodiode and/or a phototransistor, and be applied to an image sensor and/or a solar cell.

The image sensor including a photodiode requires higher resolution and accordingly a smaller pixel. At present, a silicon photodiode is widely used, but the sensitivity of the silicon photodiode may be deteriorated because it has a smaller absorption area due to smaller pixels. Accordingly, an organic photoelectric material that is capable of replacing silicon has been researched.

The organic photoelectric material has a relatively high extinction coefficient and selectively absorbs light of a particular wavelength region depending on a molecular structure, and thus may simultaneously replace a photodiode and a color filter, thereby improving sensitivity and contributing to higher integration.

SUMMARY

Example embodiments provide an organic photoelectric material being capable of selectively absorbing light of a green wavelength region and improving efficiency. Example embodiments also provide an organic photoelectric device including the organic photoelectric material. Example embodiments also provide an image sensor including the organic photoelectric device.

According to example embodiments, an organic photoelectric material is represented by the following Chemical Formula 1.

[Chemical Formula 1]

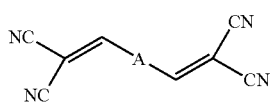

In Chemical Formula 1, A is a thiophene-containing aromatic group including 4 to 7 rings fused to one another. The A may include at least two thiophenes. The A may include a heteroatom-containing ring. The heteroatom may include nitrogen (N), silicon (Si), oxygen (O), selenium (Se), or a combination thereof.

The organic photoelectric material may be represented by at least one of the following Chemical Formulae 2 to 7.

[Chemical Formula 2]

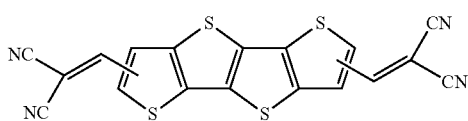

[Chemical Formula 3]

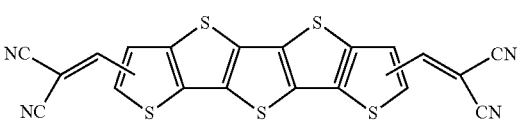

[Chemical Formula 4]

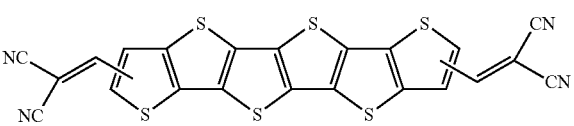

[Chemical Formula 5]

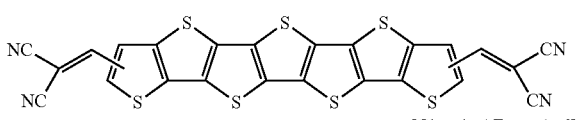

[Chemical Formula 6]

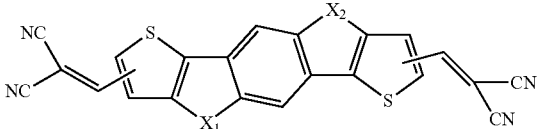

[Chemical Formula 7]

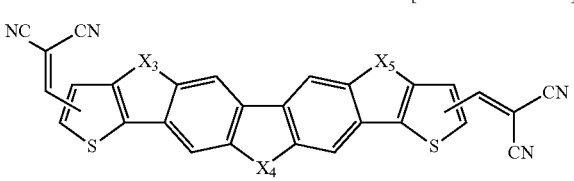

In Chemical Formulae 2 to 7,
$X_1$ to $X_5$ are the same or different and are independently $CR^1R^2$, $SiR^3R^4$, $NR^5$, oxygen (O), or selenium (Se), wherein $R^1$ to $R^5$ are the same or different and are independently hydrogen, a substituted or unsubstituted $C_1$ to $C_{20}$ alkyl group, a substituted or unsubstituted $C_6$ to $C_{20}$ aryl group, a substituted or unsubstituted $C_3$ to $C_{20}$ heteroaryl group, or a combination thereof.

The organic photoelectric material may selectively absorb light of a green wavelength region. The organic photoelectric material may have a maximum absorption peak in a wavelength region of about 500 nm to about 600 nm. The organic photoelectric material may have a band gap ranging from about 2.0 eV to about 3.0 eV.

According to example embodiments, an organic photoelectric device may include a first electrode and a second electrode facing each other and an active layer between the first electrode and the second electrode, the active layer including the organic photoelectric material represented by the above Chemical Formula 1.

According to example embodiments, an image sensor may include the organic photoelectric device.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
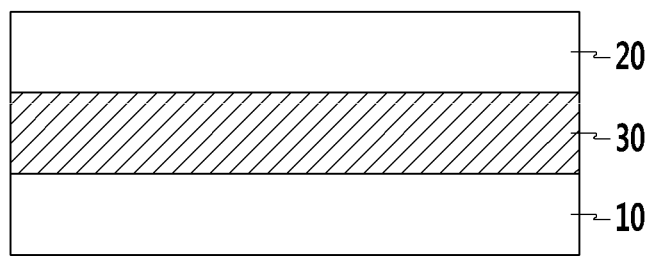
FIG. 1 is a cross-sectional view showing an organic photoelectric device according to example embodiments.

The present disclosure will be described more fully hereinafter with reference to the accompanying drawings, in which example embodiments are shown. This disclosure may, however, be embodied in many different forms and is not construed as limited to the example embodiments set forth herein.

As used herein, when a specific definition is not otherwise provided, the term 'substituted' refers to one substituted with at least one substituent including a halogen (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_4$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof in place of at least one hydrogen of a compound.

As used herein, when a specific definition is not otherwise provided, the term 'hetero' may refer to one including 1 to 3 heteroatoms selected from N, O, S, and P.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Parts having no relationship with the description are omitted for clarity, and the same or similar constituent elements are indicated by the same reference numeral throughout the specification.

It will be understood that, although the terms "first", "second", etc. may be used herein to describe various elements, components, regions, layers and/or sections, these elements, components, regions, layers and/or sections are not to be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments are not to be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, is to be interpreted as having a meaning that is consistent with their meaning in the context of the relevant art and will not be interpreted in an idealized or overly formal sense unless expressly so defined herein.

According to example embodiments, an organic photoelectric material may include a compound represented by the following Chemical Formula 1.

[Chemical Formula 1]

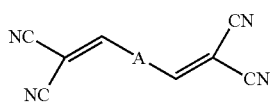

In Chemical Formula 1,

A is a thiophene-containing aromatic group including 4 to 7 rings fused to each other, the A may include at least two thiophenes and at least one of the rings may include a heteroatom, and the heteroatom may include nitrogen (N), silicon (Si), oxygen (O), selenium (Se), or a combination thereof.

The compound may have a thiophene-containing aromatic group including 4 to 7 rings at the core, and selectively absorbs light of a green wavelength region. Particularly, the 4 to 7 rings are all fused together and thus may decrease conformational torsion of the compound and increase light absorption in a narrow wavelength region, that is, sharply in a wavelength region ranging from about 500 nm to about 600 nm, without dispersing the absorption wavelength region.

In addition, the compound has a dicyanovinyl group as an electron acceptor at both ends thereof, and thus may increase a LUMO level, decrease a HOMO level and resultantly decrease a band gap. For example, the compound may have a band gap ranging from about 2.0 eV to 3.0 eV. Accordingly, the compound may effectively absorb light of a wavelength region ranging from about 500 nm to 600 nm by adjusting its energy level and thus may have high external quantum efficiency (EQE) and improved photoelectric conversion efficiency.

The organic photoelectric material may, for example, include at least one of the compounds represented by the following Chemical Formulae 2 to 7.

[Chemical Formula 2]

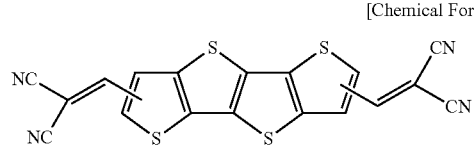

[Chemical Formula 3]

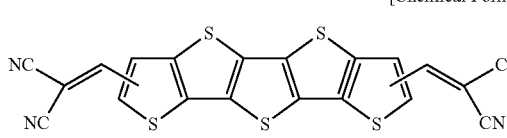

[Chemical Formula 4]

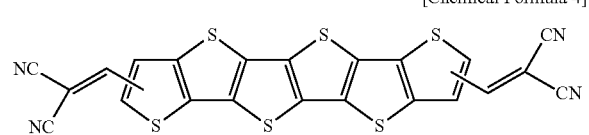

[Chemical Formula 5]

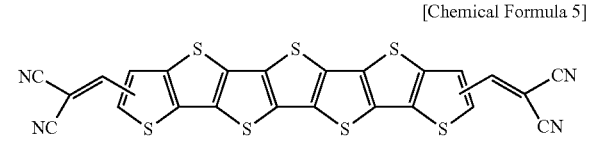

[Chemical Formula 6]

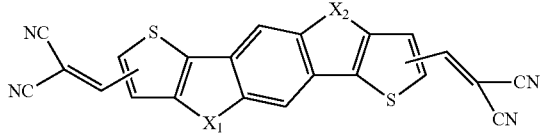

[Chemical Formula 7]

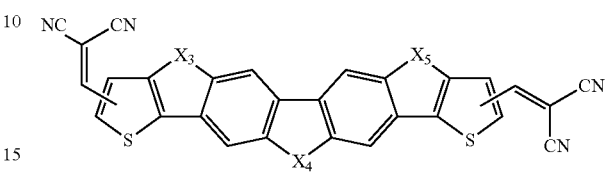

In Chemical Formulae 2 to 7, $X_1$ to $X_5$ are the same or different and are independently $CR^1R^2$, $SiR^3R^4$, $NR^5$, oxygen (O), or selenium (Se), wherein $R^1$ to $R^5$ are the same or different and are independently hydrogen, a substituted or unsubstituted $C_1$ to $C_{20}$ alkyl group, a substituted or unsubstituted $C_6$ to $C_{20}$ aryl group, a substituted or unsubstituted $C_3$ to $C_{20}$ heteroaryl group, or a combination thereof.

FIG. 1 is a cross-sectional view showing an organic photoelectric device according to example embodiments.

Referring to FIG. 1, an organic photoelectric device according to example embodiments may include a first electrode (e.g., an anode) 10 and a second electrode (e.g., a cathode) 20, and an active layer 30 interposed between the first electrode 10 and the second electrode 20. In FIG. 1, the first electrode 10 is positioned under the active layer 30, while the second electrode 20 is positioned on the active layer 30. However, the second electrode 20 may be positioned under the active layer 30 and the first electrode 10 may be positioned on the active layer 30 in an opposite way.

Either one of the first electrode 10 and second electrode 20 may be made of, for example, a transparent conductor, e.g., indium tin oxide (ITO), indium zinc oxide (IZO), aluminum-doped zinc oxide (AZO), and gallium-doped zinc oxide (GZO), while the other may be made of, for example, an opaque conductor, e.g., aluminum (Al), copper (Cu), titanium (Ti), gold (Au), silver (Ag), chromium (Cr), titanium (Ti), an alloy thereof, or a combination thereof.

The active layer 30 may transform light into an electrical signal by using photoelectric effects, and includes the aforementioned organic photoelectric material.

The active layer 30 includes the aforementioned organic photoelectric material, and may selectively absorb light of a green wavelength region and have a maximum absorption peak in a wavelength region of about 500 nm to about 600 nm in the absorption spectrum. In addition, the active layer 30 has a relatively small band gap ranging from about 2.0 eV to 3.0 eV as aforementioned, and may effectively absorb light in the wavelength region.

The organic photoelectric material may be included in a p payer, an i layer, an n layer, or a combination thereof. The p layer may be formed to be adjacent to the first electrode 10, the n layer may be formed to neighbor the second electrode 20, and the i layer may be formed to be adjacent to the p layer and the n layer. However, example embodiments are not limited thereto, and the i layer may be formed to be adjacent to the first electrode 10 and the second electrode 20 when the p layer and the n layer are not formed.

The organic photoelectric material may be included in the p payer, the i layer, the n layer, or a combination thereof.

Herein, the p layer includes a p-type material, and holes separated from excitons produced in the i layer are delivered thereto. The n layer includes an n-type material, and electrons separated from excitons produced from the i layer are delivered thereto. The i layer includes both of p-type and n-type materials and forms a pn junction, and also externally receives light, produces excitons, and separates the excitons into holes and electrons.

For example, when a compound represented by the above Chemical Formula 1 may be used as a p-type material, a material having a lower LUMO level than the compound may be used as an n-type material. Herein, the compound may be included in the p layer, the i layer, or a combination thereof. The n-type material may be included in the n layer, the i layer, or a combination thereof.

For another example, when a compound represented by the above Chemical Formula 1 may be used as an n-type material, a material having a higher LUMO level than the compound may be used as a p-type material. Herein, the compound may be included in the n layer, the i layer, or a combination thereof, and the p-type material may be included in the p layer, the i layer, or a combination thereof.

The i layer may include a bulk heterojunction (BHJ), an organic/inorganic hybrid, or a combination thereof, without limitation.

The bulk heterojunction may include at least two selected from a compound represented by the above Chemical Formula 1, polyaniline, polypyrrole, polythiophene, poly(p-phenylene vinylene), MEH-PPV (poly[2-methoxy-5-(2'-ethylhexyloxy)-1,4-phenylene vinylene), MDMO-PPV (poly(2-methoxy-5-(3,7-dimethyloctyloxy)-1,4-phenylene-vinylene)), pentacene, PEDOT (poly(3,4-ethylene dioxythiophene)), poly(3-allylthiophene), phthalocyanine, triarylamine, benzidine, pyrazoline, styrylamine, hydrazone, carbazole, thiophene, pyrrole, phenanthrene, tetracene, naphthalene, fullerene (C60, C70, C74, C76, C78, C82, C84, C720, and C860), PCBM (1-(3-methoxy-carbonyl)propyl-1-phenyl(6,6)C61), C71-PCBM, C84-PCBM, bis-PCBM, perylene, a derivative thereof, and a combination thereof, without limitation. When the bulk heterojunction is formed by using materials having different energy levels, the material having a relatively lower LUMO level may be used as an n-type material, while the other material having a higher LUMO level may be used as a p-type material.

The organic/inorganic hybrid layer may include an organic material selected from the compound represented by the above Chemical Formula 1, polyaniline, polypyrrole, polythiophene, poly(p-phenylene vinylene), MEH-PPV (poly[2-methoxy-5-(2'-ethyl-hexyloxy)-1,4-phenylene]vinylene), MDMO-PPV (poly(2-methoxy-5-(3,7-dimethyloctyloxy)-1, 4-phenylene-vinylene)), pentacene, PEDOT (poly(3,4-ethylene dioxythiophene)), poly(3-alkylthiophene), phthalocyanine, triarylamine, bezidine, pyrazoline, styrylamine, hydrazone, carbazole, thiophene, pyrrole, phenanthrene, tetracene, naphthalene, fullerene (C60, C70, C74, C76, C78, C82, C84, C720, and C860), PCBM (1-(3-methoxy-carbonyl)propyl-1-phenyl(6,6)C61), C71-PCBM, C84-PCBM, bis-PCBM, perylene, a derivative thereof, and a combination thereof, and an inorganic semiconductor selected from CdS, CdTe, CdSe, ZnO, and a combination thereof, without limitation. When the organic/inorganic hybrid layer is formed using materials having different energy levels, the material having a lower LUMO level may be used as an n-type material, while the other material having a higher LUMO level may be used as a p-type material.

When the i layer forms a photoactive layer with the p layer, the n layer, and a combination thereof, the p-type material for the i layer may be used for the p layer, while the n-type material for the i layer may be used for the n layer. However, example embodiments are not limited thereto, and the p-type material used for the i layer may be different from the material for the p layer, while the n-type material used for the i layer may be different from the material for the n layer.

The active layer 30 may have a thickness of about 1 nm to about 500 nm. When the active layer 30 has a thickness within the range, the active layer 30 may effectively absorb light, more easily separate holes from electrons, and more easily transfer the separated holes and electrons, and thus improve photoelectric conversion efficiency. The active layer 30 may have a thickness ranging from about 5 nm to 300 nm within the range, for example, a thickness ranging from about 10 nm to 200 nm within the range.

The organic photoelectric device produces excitons when the active layer 30 absorbs light of a green wavelength region entering from the first electrode 10 and/or the second electrode 20. The excitons are separated into holes and electrons in the active layer 30. The separated holes move toward the first electrode 10 while the electrons move toward the second electrode 20, thereby forming a current in the organic photoelectric device.

Herein, an auxiliary layer (not shown) is further included between the first electrode 10 and the active layer 30 and/or between the second electrode 20 and the active layer 30 in order to more easily move the holes and electrons separated in the active layer 30.

The auxiliary layer may include one selected from a hole transport layer (HTL), an electron blocking layer (EBL), an electron transport layer (ETL), and a hole blocking layer (HBL).

The hole transport layer (HTL) may play a role of facilitating transportation of holes, and may include one selected from, for example, PEDOT:PSS (poly(3,4-ethylene dioxythiophene):poly(styrene sulfonate)), polyarylamine, poly(N-vinylcarbazole), polyaniline, polypyrrole, TPD (N,N,N',N'-tetrakis(4-methoxyphenyl)-benzidine), α-NPD (4-bis[N-(1-naphthyl)-N-phenyl-amino]piphenyl), m-MTDATA, TCTA (4,4',4"-tris(N-carbazolyl)-triphenylamine), and a combination thereof, without limitation.

The electron blocking layer (EBL) may play a role of prohibiting transportation of electrons and may include one selected from, for example, PEDOT:PSS (poly(3,4-ethylene dioxythiophene):poly(styrene sulfonate)), polyarylamine, poly(N-vinylcarbazole), polyaniline, polypyrrole, TPD (N,N,N',N'-tetrakis(4-methoxyphenyl)-benzidine), α-NPD (4-bis[N-(1-naphthyl)-N-phenyl-amino]piphenyl), m-MTDATA, TCTA (4,4',4"-tris(N-carbazolyl)-triphenylamine), and a combination thereof, without limitation.

The electron transport layer (ETL) may play a role of facilitating transportation of electrons, and may include one selected from, for example, NTCDA (1,4,5,8-naphthalene-tetracarboxylic dianhydride), BCP (bathocuproine), LiF, $Alq_3$, $Gaq_3$, $Inq_3$, $Znq_2$, $Zn(BTZ)_2$, $BeBq_2$, and a combination thereof, without limitation.

The hole blocking layer (HBL) may play a role of prohibiting transportation of holes, and may include one selected from NTCDA (1,4,5,8-naphthalene-tetracarboxylic dianhydride), BCP (bathocuproine), Li F, $Alq_3$, $Gaq_3$, $Inq_3$, $Znq_2$, $Zn(BTZ)_2$, $BeBq_2$, and a combination thereof, without limitation.

The organic photoelectric device may be applied to various fields, for example a solar cell, an image sensor, a photodetector, a photo-sensor, and an organic light emitting diode (OLED). Particularly, when the organic photoelectric device is applied to an image sensor, the organic photoelectric device may simultaneously replace a color filter and thus contribute to higher integration.

The image sensor includes a pixel array in which a plurality of pixels are arranged in a matrix format, and each pixel may include the aforementioned organic photoelectric device. The organic photoelectric device may sense light and transfer the sensed information to a transistor.

Hereinafter, the present disclosure is illustrated in more detail with reference to examples. However, these embodiments are examples, and the present disclosure is not limited thereto.

Preparation of Organic Photoelectric Material

Synthesis Example 1

A compound represented by the following Chemical Formula 3A is prepared.

[Chemical Formula 3A]

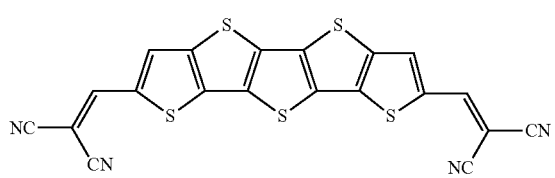

Synthesis Example 2

A compound represented by the following Chemical Formula 4A is prepared.

[Chemical Formula 4A]

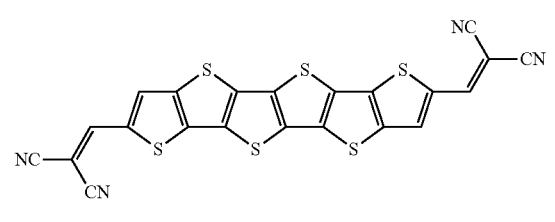

Synthesis Example 3

A compound represented by the following Chemical Formula 5A is prepared.

[Chemical Formula 5A]

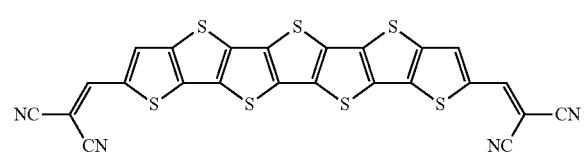

Synthesis Example 4

A compound represented by the following Chemical Formula 3A is prepared.

[Chemical Formula 6A]

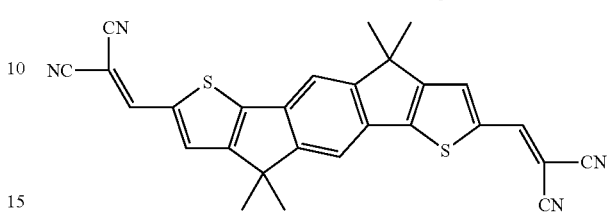

First Step:

In a 2 L 3-neck round bottom flask, 500 ml of toluene is degassed and charged with $N_2$ three times, then 33.4 g (0.0879 mol, 1 eq) of 2.5-dibromoterephthalate (TCI) and 49 g (0.3517 mol, 4 eq) of $K_2CO_3$ are added. The reaction suspension is degassed and charged with $N_2$ once then added with 7.2 g (0.0088 mol, 0.1 eq) of $PdCl_2$ (dppf) DCM (Sigma-Aldrich Co. Ltd.). Next, the reactant is degassed and charged with $N_2$ once then heated at 60° C. for 2 hours. Then, 45 g (0.3517 mol, 4 eq) of thiophene-2-boronic acid is added to the reactant. The mixture is heated at 110° C. for 16 hours. When diethyl 2.5-dibromoterephthalate still remains in the reactant, 23 g (2 eq) of thiophene-2-boronic acid is further added thereto, and 12 g (1 eq) of the thiophene-2-boronic acid is further added thereto after 40 hours. The reaction mixture is heated at reflux for 8 hours until reaction completion is observed on TLC analysis, cooled down to room temperature, and 500 ml of $H_2O$ is added thereto. The resulting reaction mixture is extracted with 500 ml of methylene chloride (MC) (4×), dried using $MgSO_4$, and then filtered through celite. Then, column chromatography (elution: a mixture of hexane and ethylacetate) is used to remove impurities from the reactant, obtaining 20.4 g of a yellow solid, and obtaining the following compound A. The compound has a yield of 60%.

Reaction Scheme 1

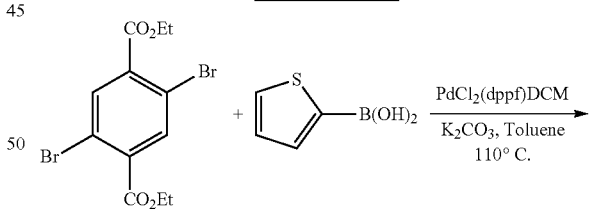

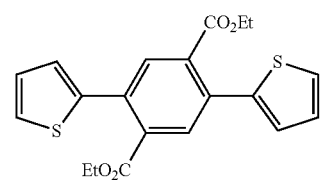

Second Step:

20 g (0.0517 mol, 1.0 eq) of the compound A is put in 200 ml of dry ethanol, and 190 ml (0.7038 mol, 14 eq) of 3.75 N NaOH is added thereto. The mixture is refluxed for 15 hours. The reactant is cooled down to room temperature, and the ethanol is removed therefrom by a rotary evaporator. Then, the aqueous residue is cooled down in an ice bath, and 150 ml of 6 N HCl is added thereto. The mixture is stirred for one hour. The reactant is filtered and cleaned with H₂O, obtaining a sticky solid. The sticky solid is dissolved in a mixed solvent of 400 ml of ether and 100 ml of THF and dried using MgSO₄. The dried reactant is filtered, obtaining 16 g of a yellow solid having the following compound B. The compound has a yield of 93%.

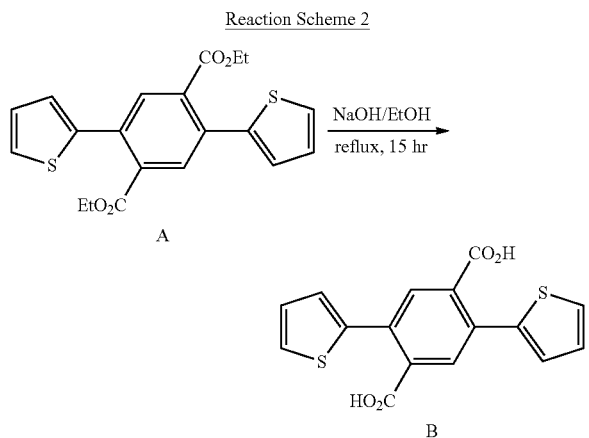

Third Step:

16 g (0.0484 mol, 1 eq) of the compound B is dissolved in 800 ml of methylene chloride, and 17 ml (0.1937 mol, 4 eq) of oxalyl chloride is added thereto. Next, the reactant is cooled down in an ice bath. Then, 7.5 ml (0.0969 mol, 2 eq) of DMF is added to the reactant drop by drop for 45 minutes. The resulting reactant is warmed to room temperature and stirred for 22 hours. After the reaction is completed, a solvent is removed from the reactant by a rotary evaporator, thereby obtaining a yellow solid residue. The yellow solid residue is dissolved in 400 ml of methylene chloride (MC) obtaining a solution C.

Then, 32 g (0.2420 mol, 5 eq) of AlCl₃ is dissolved in 800 ml of methylene chloride, and the solution is cooled down to 0° C., obtaining a yellow suspension solution. Next, 400 ml of the solution C is added to the yellow suspension solution, obtaining a brown suspension solution. The brown suspension solution is stirred at room temperature for 24 hours, and the product is poured into ice including 1 L of 6 N HCl, obtaining a blue suspension solution. The blue suspension solution is stirred for 10 minutes, and 1 L of ice is additionally added thereto. The mixture is filtered, thereby obtaining a blue solid. The blue solid is cleaned with 500 ml of 2 N HCl, 500 ml of H₂O, and 500 ml of acetone and dried in an environment exposed to air, obtaining 14 g of a blue solid having the following compound D. The compound has a yield of 98%.

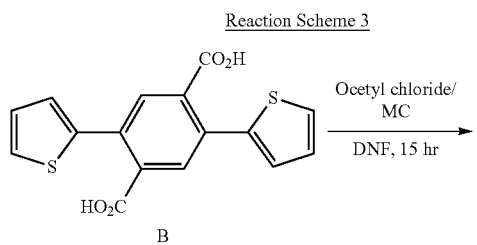

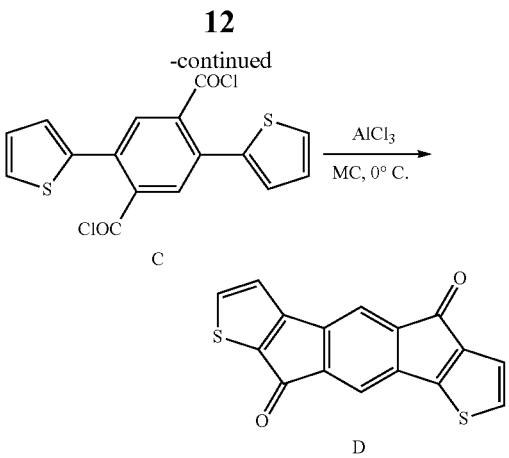

Fourth Step:

13 g (0.0442 mol, 1.0 eq) of the compound D is dissolved in 500 ml of ethylene glycol, and the solution is cooled down in an ice bath, obtaining a blue suspension solution. Next, 49.6 g (0.8833 mol, 20 eq) of KOH is added to the blue suspension solution. The mixture is stirred for 30 minutes. Then, the reactant is warmed to room temperature, and 41 ml (0.8833 mol, 20 eq) of hydrazine is added thereto. The mixture is stirred for 30 minutes, obtaining a blue mixture. The blue mixture is heated at 140° C. for 23 hours. After the reaction completion, the reaction mixture is cooled down to room temperature and poured into ice including 200 ml of 6 N HCl (pH=2). Then, the reaction mixture is extracted with 300 ml of ether and 300 ml of methylene chloride and filtered to separate a solid from a water layer. The solid is dried, filtered, and concentrated, obtaining a blue solid residue. The brown solid residue is agitated in 100 ml of methanol and then filtered, obtaining 6 g (51%) of a light yellow solid, the following compound E.

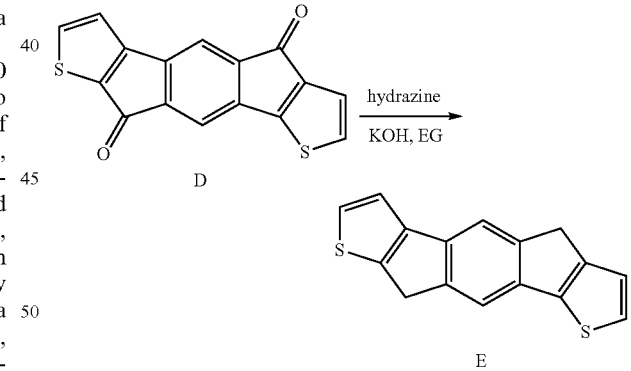

Fifth Step:

5.7 g (0.0214 mol, 1.0 eq) of the compound E is dissolved in 200 ml of distilled THF, and 19.2 g (0.1712 mol, 8 eq) of potassium t-butoxide (t-BuOK) is added thereto, obtaining a bluish green suspension solution. The bluish green suspension solution is heated at 60° C. for 1 hour and cooled down to room temperature, obtaining a black suspension solution. Next, 11 ml (0.1712 mol, 8 eq) of iodomethane is added to the black suspension solution drop by drop, obtaining a black mixture. The black mixture is stirred at room temperature for 24 hours. After the reaction completion, the reaction mixture is cooled down in an ice bath, and 30 ml of NH₄OH is added thereto. The mixture is stirred for 15 minutes. Then, 500 ml of water is added to the reaction mixture, and the resulting mixture is extracted with 300 ml of ether and 300 ml of methylene chloride. The extract is dried with MgSO$_4$, filtered, and concentrated, obtaining a black residue. The black residue is dissolved in 200 ml of methylene chloride, and the solution is filtered using column chromatography (eluting solution: hexane), obtaining 6 g of a brownish yellow solid, the following compound F. The compound has a yield of 86%.

Reaction Scheme 5

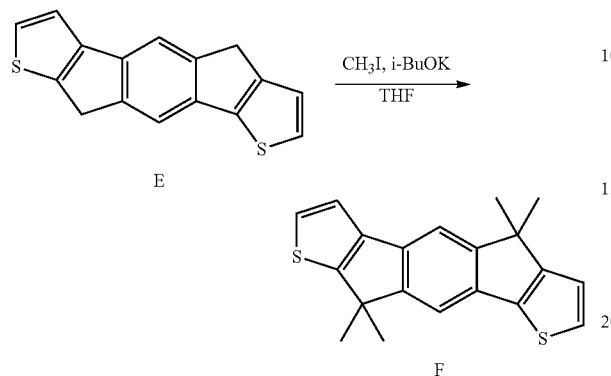

Sixth Step:

6 g (0.0186 mol, 1 eq) of the compound F is dissolved in 250 ml of 1,2-dichloroethane, and a solution of 9 ml (0.0930 mol, 5 eq) of POCl$_3$ and 7.2 ml (0.0930 mol, 5 eq) of DMF is added thereto, obtaining a reddish orange solution. The reddish orange solution is refluxed for 24 hours, obtaining an orange suspension solution. The orange suspension solution is cooled down to room temperature, and 100 ml of methylene chloride is added thereto. The mixture is poured into 1 L of saturated sodium acetate. The resulting mixture is stirred for 2 hours. Next, a methylene chloride layer is separated from the reactant, and the remaining water layer is extracted with 200 ml of methylene chloride, dried using MgSO$_4$, and then filtered and concentrated. The resulting product is then filtered using column chromatography (eluting solution: hexane, ethylacetate, and methylene chloride), obtaining 6.2 g of a yellow-orange solid. The compound has a yield of 88%.

Reaction Scheme 6

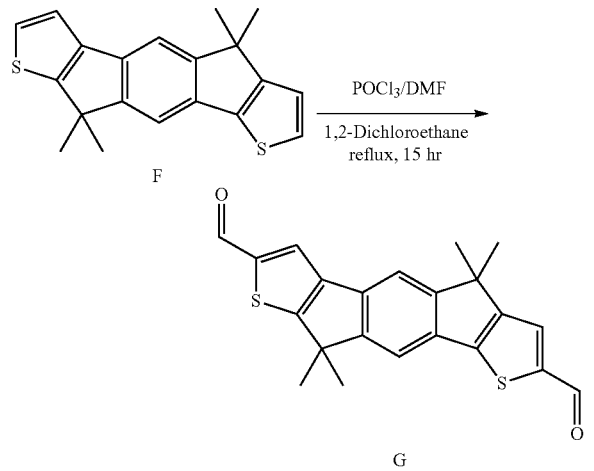

Seventh Step:

8.4 g (0.1268 mol, 8 eq) of malononitrile is dissolved in 200 ml of chloroform, and 6 g (0.0159 mol, 1.0 eq) of the compound G is added thereto, obtaining a brownish yellow solution. Next, 0.7 ml (0.0048 mol, 0.3 eq) of TEA is added to the brownish yellow solution drop by drop, obtaining a maroon suspension solution. The maroon suspension solution is refluxed at 64° C. for 10 hours. After the reaction completion, the reaction mixture is cooled down to room temperature, and 300 ml of methylene chloride and 500 ml of water are added thereto. The mixture is extracted with 500 ml of methylene chloride, and the extract is dried with MgSO$_4$. Then, the resulting product is filtered using column chromatography (eluting solution: hexane and ethylacetate), obtaining 3.22 g of a red solid, a compound H represented by Chemical Formula 6A. The compound has a yield of 43%.

Reaction Scheme 7

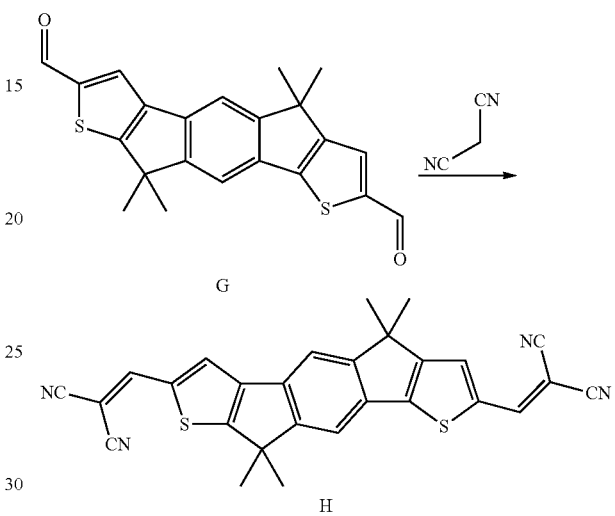

The compound H (Chemical Formula 6A) has NMR (400 MHz, DMSO-d6) data as follows.

8.67 (s, 2H), 8.19 (s, 2H), 8.00 (s, 2H), 1.53 (s, 12H)

Synthesis Example 5

A compound represented by the following Chemical Formula 6B is prepared.

[Chemical Formula 6B]

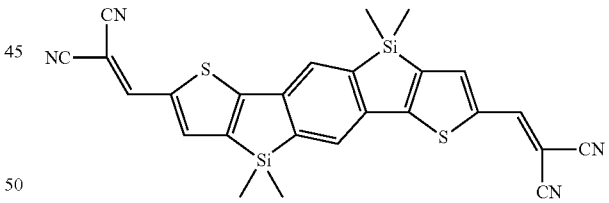

Synthesis Example 6

A compound represented by the following Chemical Formula 7A is prepared.

[Chemical Formula 7A]

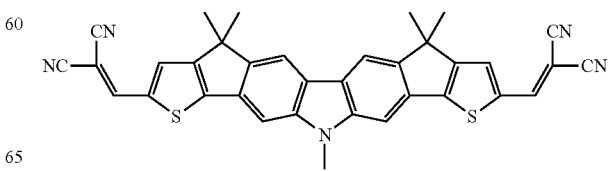

Comparative Synthesis Example 1

A compound represented by the following Chemical Formula 8 is prepared.

[Chemical Formula 8]

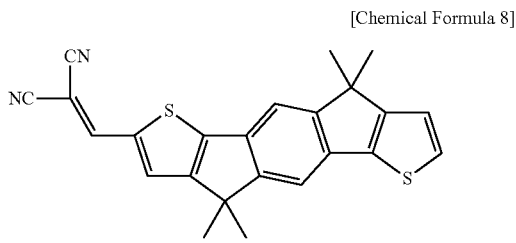 [SMILES: CC1(C)c2cc3c(cc2-c2sccc21)C(C)(C)c1cc(C=C(C#N)C#N)sc1-3]

Comparative Synthesis Example 2

A compound represented by the following Chemical Formula 9 is prepared.

[Chemical Formula 9]

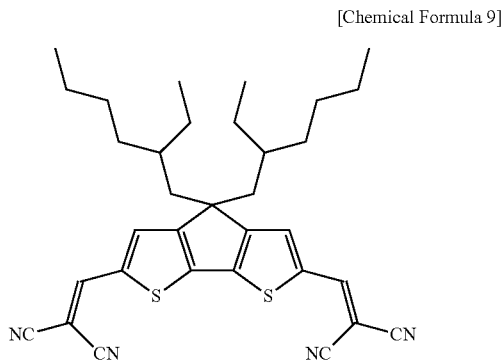 [SMILES: CCCCC(CC)CC1(CC(CC)CCCC)c2cc(C=C(C#N)C#N)sc2-c2sc(C=C(C#N)C#N)cc21]

Evaluation 1: Energy Level of Organic Photoelectric Material

The compounds according to Synthesis Examples 1 to 6 are evaluated regarding HOMO and LUMO levels and band gap.

The results are provided in Table 1.

TABLE 1

|  | HOMO level (eV) | LUMO level (eV) | Band gap (eV) |
| --- | --- | --- | --- |
| Synthesis Example 1 | 6.24 | 3.67 | 2.57 |
| Synthesis Example 2 | 6.11 | 3.61 | 2.50 |
| Synthesis Example 3 | 5.99 | 3.54 | 2.45 |
| Synthesis Example 4 | 5.99 | 3.43 | 2.56 |
| Synthesis Example 5 | 6.03 | 3.38 | 2.65 |
| Synthesis Example 6 | 5.74 | 3.19 | 2.55 |

Referring to Table 1, the compounds according to Synthesis Examples 1 to 6 have a band gap ranging from about 2.0 to 3.0 eV, for example, about 2.0 to 2.7 eV.

Evaluation 2: Light Absorption Properties of Organic Photoelectric Material

The compounds according to Synthesis Examples 1 to 6 are evaluated regarding light absorption properties according to wavelength.

Figure 2:
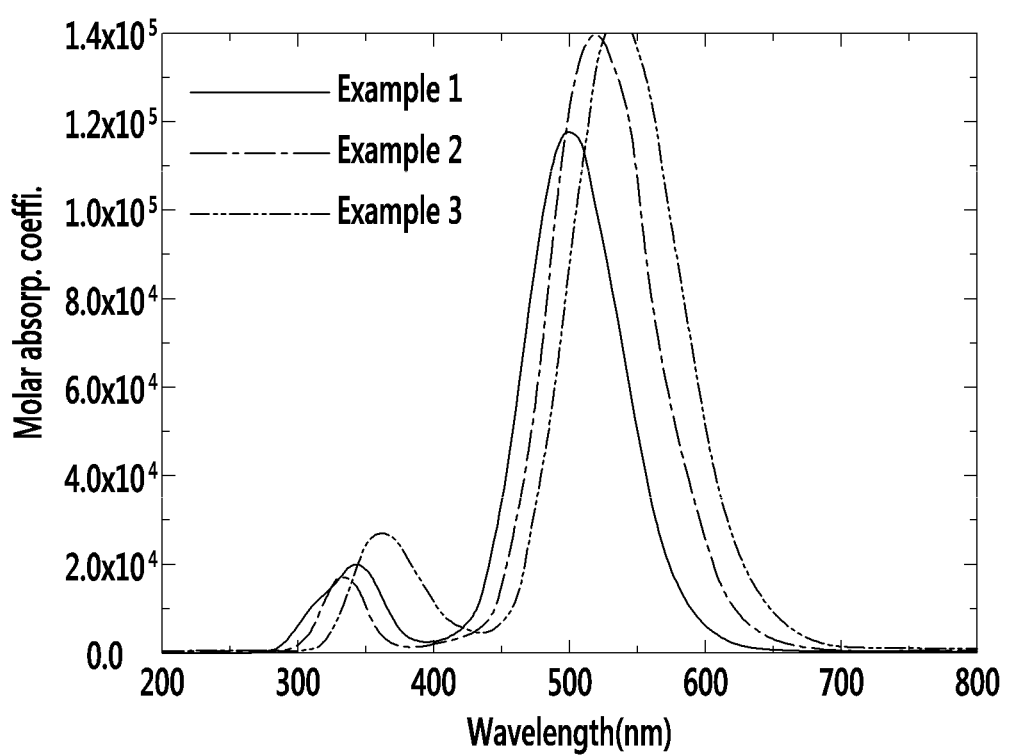
FIG. 2 is a graph showing extinction coefficients according to wavelengths of compounds according to Synthesis Examples 1 to 3.
Figure 3:
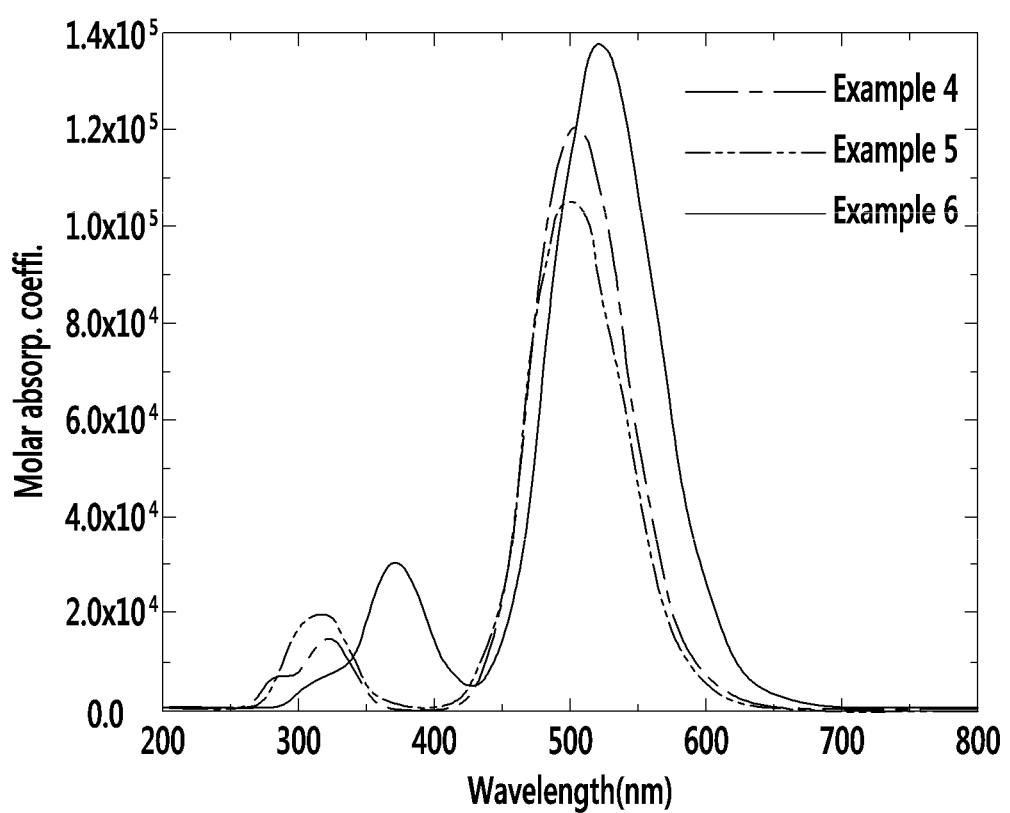
FIG. 3 is a graph showing extinction coefficients according to wavelengths of compounds according to Synthesis Examples 4 to 6.
Figure 4:
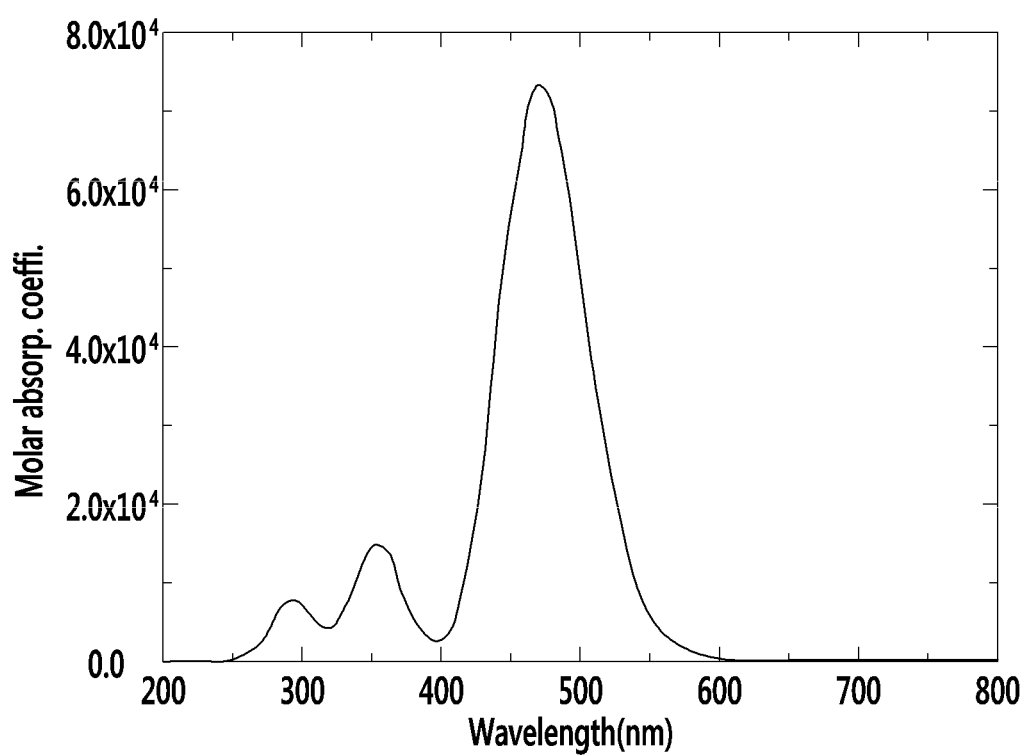
FIG. 4 is a graph showing extinction coefficients according to wavelengths of a compound according to Comparative Synthesis Example 1.
Figure 5:
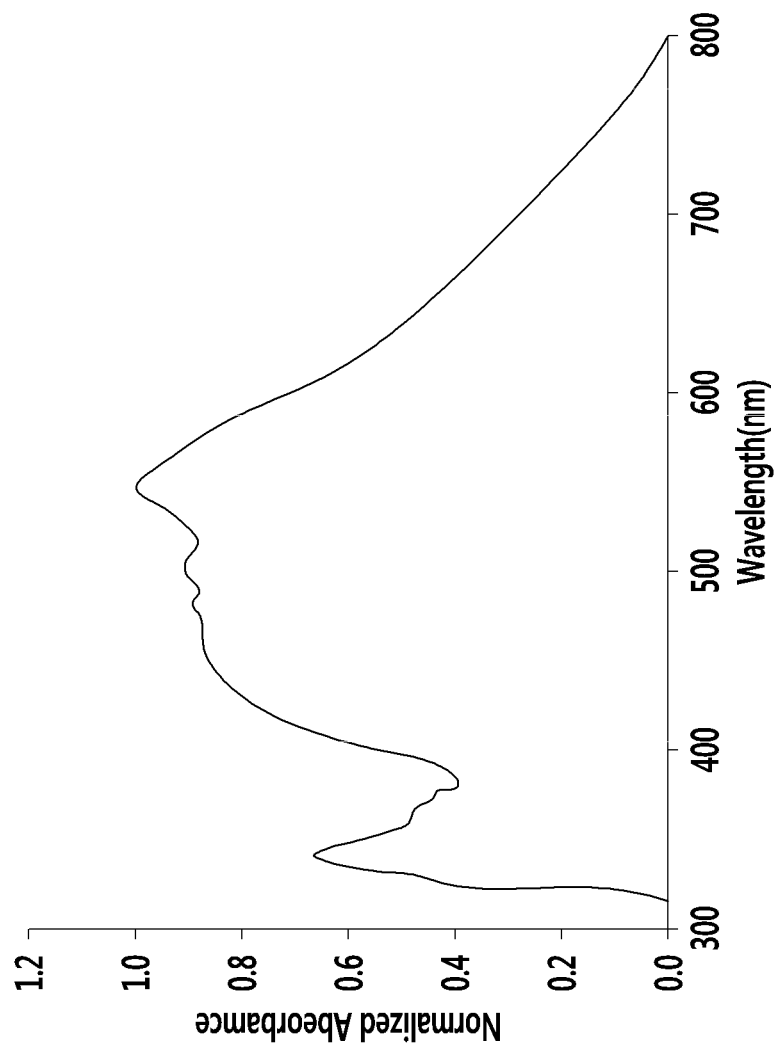
FIG. 5 is a graph showing extinction coefficients according to wavelengths of a compound according to Comparative Synthesis Example 2.

FIG. 2 is a graph showing extinction coefficients according to wavelengths of the compounds according to Synthesis Examples 1 to 3, FIG. 3 is a graph showing extinction coefficients according to wavelengths of the compounds according to Synthesis Examples 4 to 6, FIG. 4 is a graph showing extinction coefficients according to wavelengths of the compound according to Comparative Synthesis Example 1, and FIG. 5 is a graph showing extinction coefficients according to wavelengths of the compound according to Comparative Synthesis Example 2.

Referring to FIGS. 2 and 3, the compounds according to Synthesis Examples 1 to 6 have a maximum absorption peak in a wavelength region ranging from about 500 nm to 600 nm, and thus selectively absorb light in a green wavelength region. In addition, the compounds have a sharp peak in the wavelength region and thus may improve sensitivity and color purity.

On the contrary, referring to FIG. 4, the compound according to Comparative Synthesis Example 1 has a maximum absorption peak of less than about 500 nm but smaller absorption in a wavelength region ranging from 500 nm to 600 nm. Accordingly, the compound according to Comparative Synthesis Example 1 mainly absorbs light in a short wavelength region compared with the compounds according to Synthesis Examples 1 to 6.

In addition, referring to FIG. 5, the compound according to Comparative Synthesis Example 2 mainly absorbs light in a wavelength region ranging from about 300 nm to about 700 nm. Accordingly, the compound according to Comparative Synthesis Example 2 has deteriorated selectivity for light in a green wavelength region.

Therefore, the compounds according to Synthesis Example 1 to 6 have higher selectivity for absorbing light in a green wavelength region ranging from about 500 to 600 nm than the compounds according to Comparative Synthesis Examples 1 and 2.

Evaluation 3: Light Absorption Properties of Thin Film

The compound according to Synthesis Example 4 is fabricated into a thin film and then evaluated regarding light absorption properties according to wavelength.

The light absorption properties according to wavelength are evaluated by using the compound according to Synthesis Example 4 to form a 70 nm-thick thin film at a deposition speed of 1 Å/s in a thermal evaporator. The light absorption properties are evaluated by radiating ultraviolet (UV)-visible ray (UV-Vis) using Cary 5000 UV spectroscopy (Varian Inc.).

Figure 6:
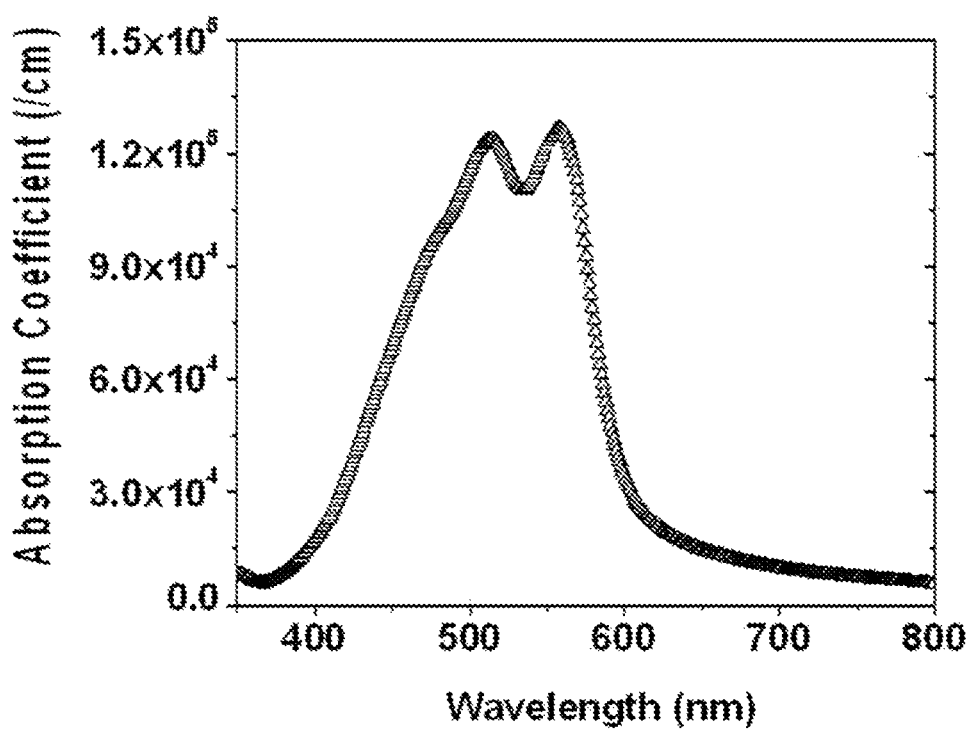
FIG. 6 is a graph showing light absorption properties of a compound according to Synthesis Example 4.

FIG. 6 is a graph showing light absorption properties of the compound according to Synthesis Example 4.

Referring to FIG. 6, a film formed of the compound according to Synthesis Example 4 has a maximum absorption peak in a wavelength region ranging from about 500 nm to 600 nm. Accordingly, the film selectively absorbs light in a green wavelength region.

Fabrication of Organic Photoelectric Device

Example 1

ITO is sputtered and laminated on a glass substrate to form an about 120 nm-thick anode, and 30 nm of MoO as a hole transport layer HTL is deposited thereon. Next, N,N'-dimethyl quinacridone (NNQA) as a p-type semiconductor material is deposited thereon to form a 35 nm-thick p-type layer. Then, the compound represented by Chemical Formula 6A according to Synthesis Example 4 as an n-type semiconductor material is thermally deposited to be a 35 nm-thick n-type layer. Then, aluminum (Al) is sputtered and laminated to fabricate an 80 nm-thick cathode, which is used to fabricate an organic photoelectric device.

Evaluation 4

The organic photoelectric device according to Example 1 is evaluated regarding external quantum efficiency (EQE) according to wavelength.

The external quantum efficiency is measured using an IPCE measurement system (McScience Inc., Korea). First, a Si photodiode (Hamamatsu, Japan) is used to calibrate the equipment, and the organic photoelectric device according to Example 1 is mounted on the equipment and then measured regarding external quantum efficiency in a wavelength region ranging from 350-750 nm.

Figure 7:
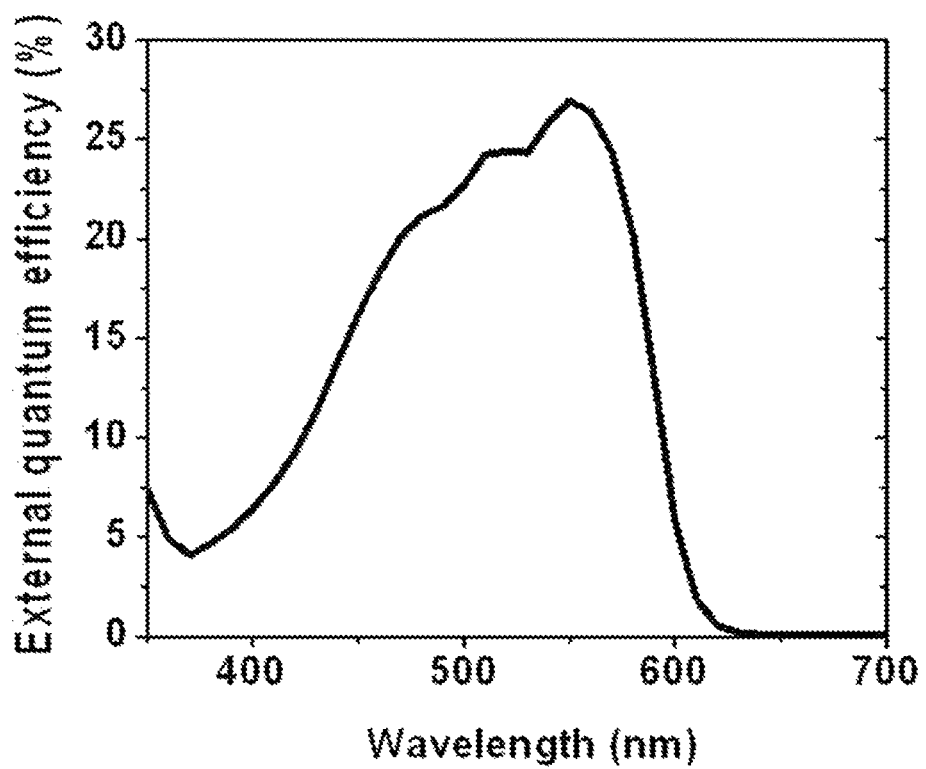
FIG. 7 is a graph showing external quantum efficiency according to a wavelength of an organic photoelectric device according to Example 1.

FIG. 7 is a graph showing external quantum efficiency according to a wavelength of the organic photoelectric device according to Example 1.

Referring to FIG. 7, the organic photoelectric device according to Example 1 has a maximum peak of external quantum efficiency (EQE) in a green wavelength region ranging from about 500 nm to 600 nm, and in particular, about 27% external quantum efficiency (EQE) at a green wavelength region of 550 nm.

Evaluation 5

The organic photoelectric device according to Example 1 is measured regarding current density while various biases are applied thereto.

Figure 8:
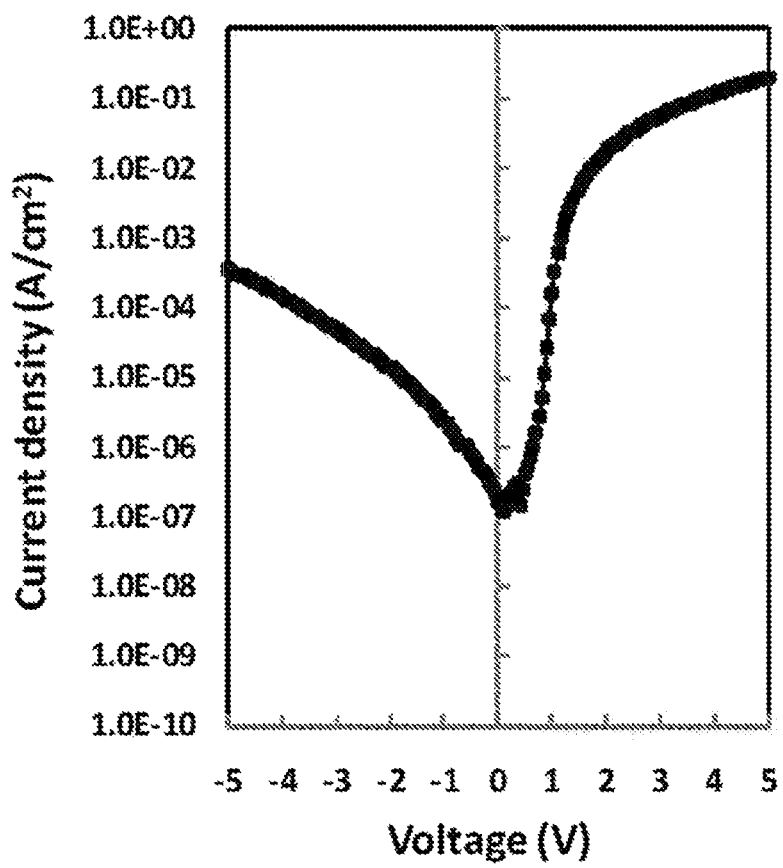
FIG. 8 is a graph showing current density of the organic photoelectric device according to Example 1 according to a voltage.

FIG. 8 is a graph showing current density according to voltage of the organic photoelectric device according to Example 1.

Referring to FIG. 8, the organic photoelectric device according to Example 1 has a diode characteristic such that current flow is suppressed in a reverse voltage direction.

Example 2

An about 120 nm-thick anode is fabricated by sputtering and laminating ITO on a glass substrate, and 30 nm of MoO as a hole transport layer HTL is deposited thereon. Next, a 90 nm-thick active layer is formed thereon by codepositing a mixture prepared by mixing dimethyl quinacridone (NNQA) as a p-type semiconductor material and a compound represented by the above Chemical Formula 6A in a composition ratio of 2:1. Then, aluminum (Al) is sputtered and laminated to fabricate an 80 nm-thick cathode, which is used to fabricate an organic photoelectric device.

Evaluation 6

The organic photoelectric device according to Example 2 is evaluated regarding external quantum efficiency (EQE) according to wavelength.

The external quantum efficiency is measured using an IPCE measurement system (McScience Inc., Korea). First, a Si photodiode (Hamamatsu, Japan) is used to calibrate equipment, and the organic photoelectric device according to Example 2 is mounted on the equipment. The organic photoelectric device is measured regarding external quantum efficiency in a wavelength region ranging from 350-750 nm.

Figure 9:
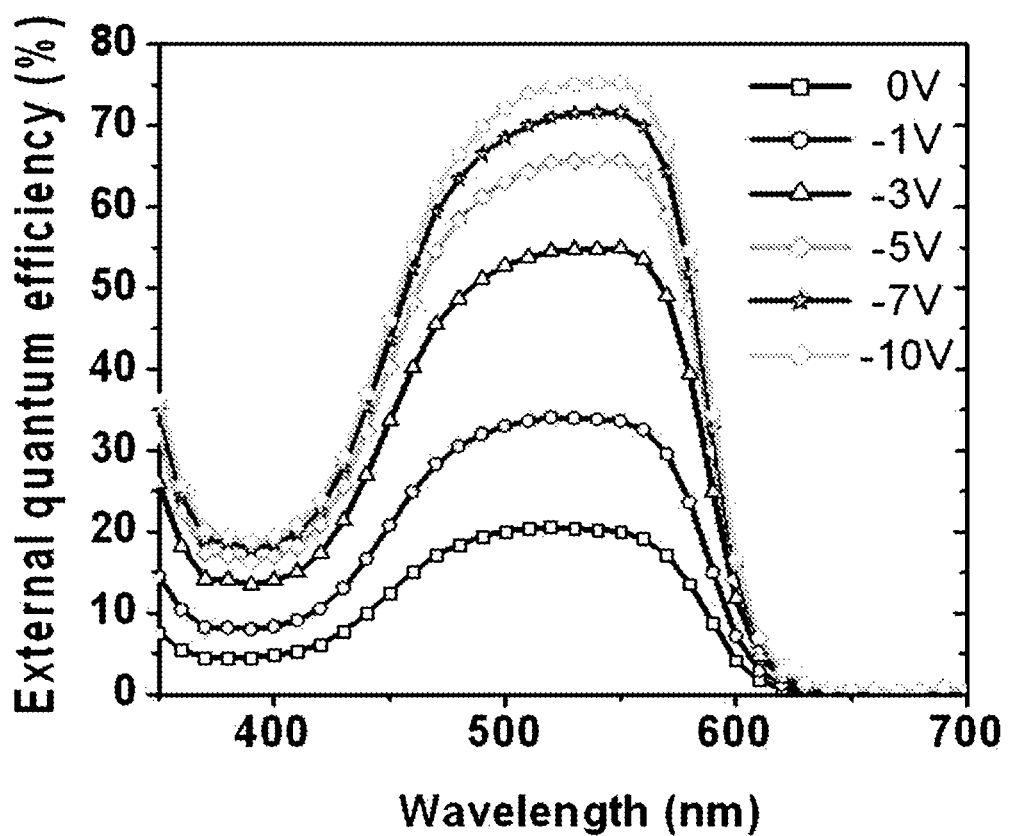
FIG. 9 is a graph showing external quantum efficiency of an organic photoelectric device according to Example 2 according to a wavelength.

FIG. 9 is a graph showing external quantum efficiency according to a wavelength of the organic photoelectric device according to Example 2.

Referring to FIG. 9, the organic photoelectric device according to Example 2 has a maximum peak of external quantum efficiency (EQE) in a green wavelength region ranging from about 500 to 600 nm, for example, external quantum efficiency (EQE) of 20.6% at a wavelength of about 550 nm.

In addition, the organic photoelectric device according to Example 2 has external quantum efficiency that is changed as various voltages are applied thereto. The organic photoelectric device according to Example 2 is a sensor selectively absorbing green light in a visible ray region and generating a current, and thus amplifies a fine signal difference by applying a voltage thereto. Referring to FIG. 9, the organic photoelectric device according to Example 2 has about 65.7% amplified efficiency without changing an external quantum efficiency graph when a voltage of −5 V is applied thereto, for example, about 55% efficiency when a low voltage of −3 V is applied thereto.

Evaluation 7

The organic photoelectric device according to Example 2 is measured regarding current density while various biases are applied thereto.

Figure 10:
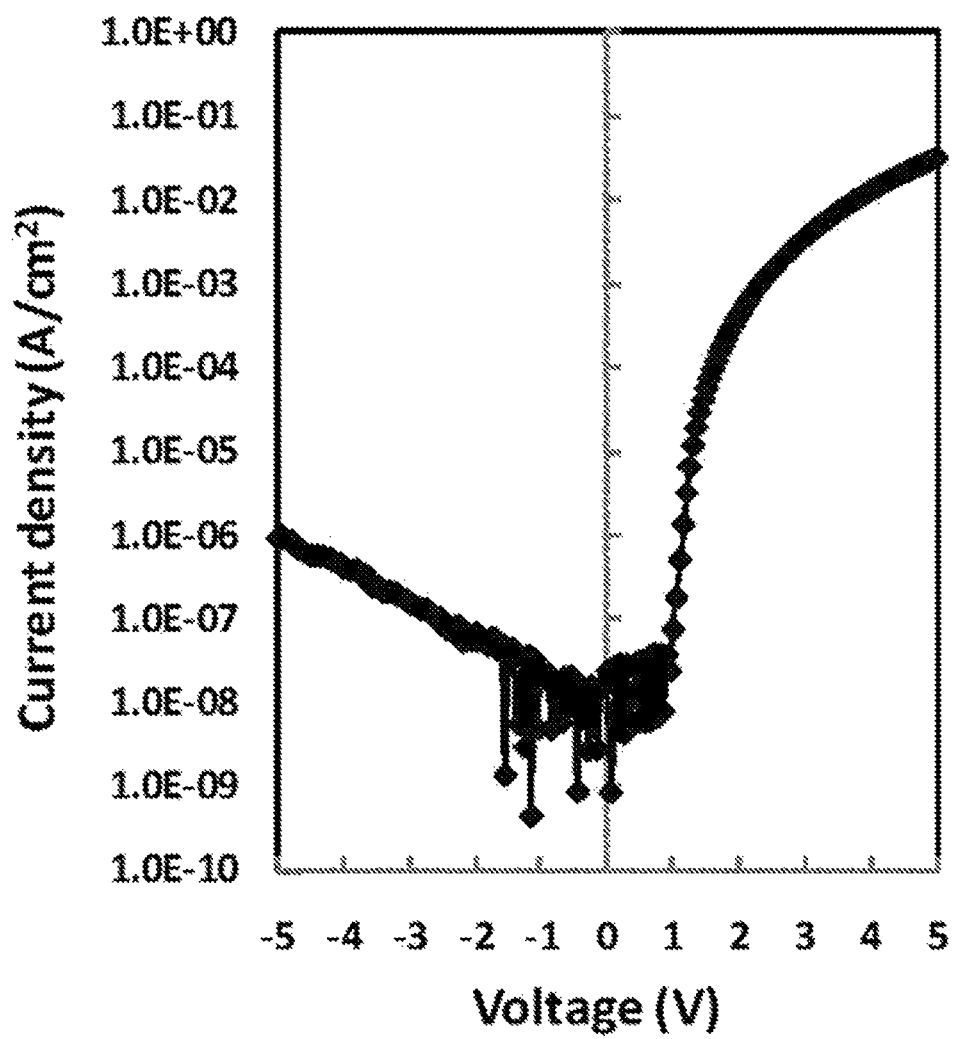
FIG. 10 is a graph showing current density of the organic photoelectric device according to Example 2 according to a voltage.

FIG. 10 is a graph showing a current density according to a voltage of the organic photoelectric device according to Example 2.

Referring to FIG. 10, the organic photoelectric device according to Example 2 has diode characteristic that suppress a current flow in a reverse voltage direction.

While this disclosure has been described in connection with what is presently considered to be practical example embodiments, it is to be understood that example embodiments are not limited to the disclosed embodiments, but, on the contrary, is intended to cover various modifications and equivalent arrangements included within the spirit and scope of the appended claims.

What is claimed is:

1. An organic photoelectric material comprising a compound represented by the following Chemical Formula 1:

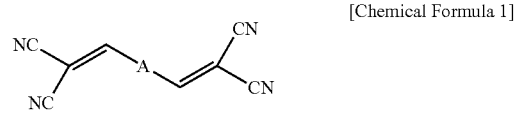

[Chemical Formula 1]

wherein, in the above Chemical Formula 1,
A is a thiophene-containing aromatic group including 4 to 7 rings fused to each other.

2. The organic photoelectric material of claim 1, wherein the A includes at least two thiophenes.

3. The organic photoelectric material of claim 1, wherein the A includes a heteroatom-containing ring.

4. The organic photoelectric material of claim 3, wherein the heteroatom includes one of nitrogen (N), silicon (Si), oxygen (O), selenium (Se), and a combination thereof.

5. The organic photoelectric material of claim 1, wherein the organic photoelectric material includes at least one of the compounds represented by the following Chemical Formulae 2 to 7:

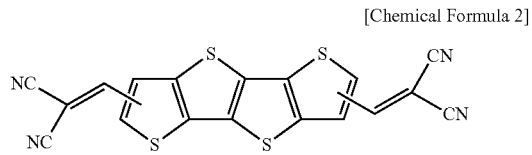

[Chemical Formula 2]

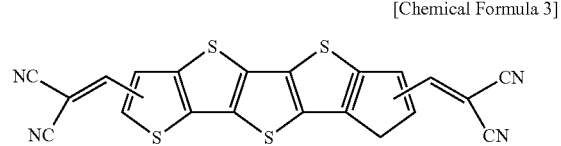

[Chemical Formula 3]

-continued

[Chemical Formula 4]

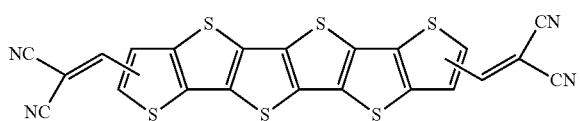

[Chemical Formula 5]

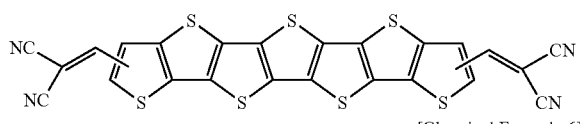

[Chemical Formula 6]

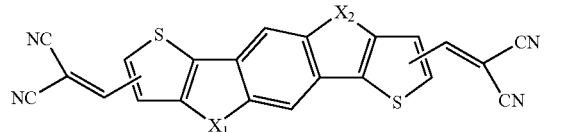

[Chemical Formula 7]

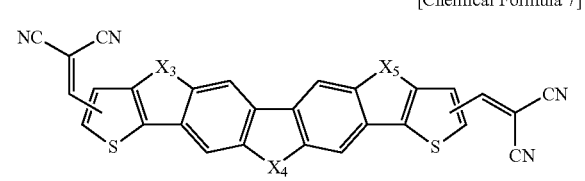

wherein, in Chemical Formulae 2 to 7,
each of $X_1$ to $X_5$ are one of the same and different and are independently one of $CR^1R^2$, $SiR^3R^4$, $NR^5$, oxygen (O), and selenium (Se), wherein each of $R^1$ to $R^5$ are the same or different and are independently one of hydrogen, a substituted or unsubstituted $C_1$ to $C_{20}$ alkyl group, a substituted or unsubstituted $C_6$ to $C_{20}$ aryl group, a substituted or unsubstituted $C_3$ to $C_{20}$ heteroaryl group, and a combination thereof.

6. The organic photoelectric material of claim 1, wherein the organic photoelectric material selectively absorbs light of a green wavelength region.

7. The organic photoelectric material of claim 1, wherein the organic photoelectric material has a maximum absorption peak in a wavelength region of about 500 nm to about 600 nm.

8. The organic photoelectric material of claim 1, wherein the organic photoelectric material has a band gap of about 2.0 eV to about 3.0 eV.

9. An organic photoelectric device, comprising:
a first electrode and a second electrode facing each other, and
an active layer between the first electrode and the second electrode, the active layer including a compound represented by the following Chemical Formula 1:

[Chemical Formula 1]

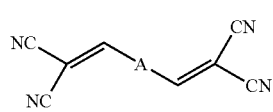

wherein, in Chemical Formula 1,
A is a thiophene-containing aromatic group including 4 to 7 rings fused one another.

10. The organic photoelectric device of claim 9, wherein the A includes at least two thiophenes.

11. The organic photoelectric device of claim 9, wherein the A includes a heteroatom-containing ring.

12. The organic photoelectric device of claim 11, wherein the heteroatom includes one of nitrogen (N), silicon (Si), oxygen (O), selenium (Se), and a combination thereof.

13. The organic photoelectric device of claim 9, wherein the active layer includes at least one of the compounds represented by the following Chemical Formulae 2 to 7:

[Chemical Formula 2]

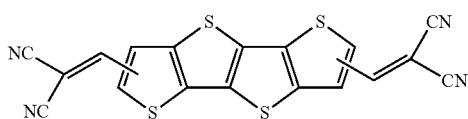

[Chemical Formula 3]

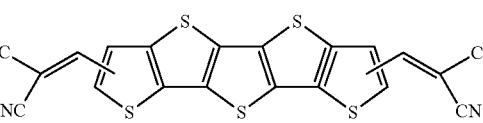

[Chemical Formula 4]

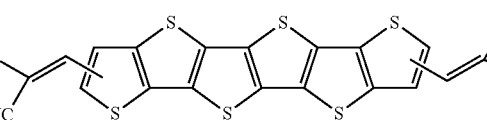

[Chemical Formula 5]

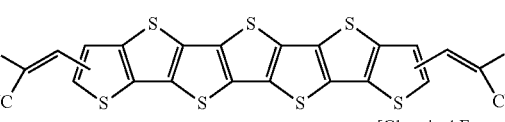

[Chemical Formula 6]

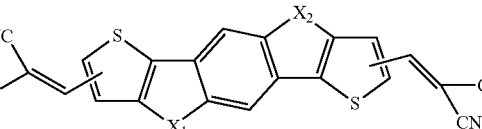

[Chemical Formula 7]

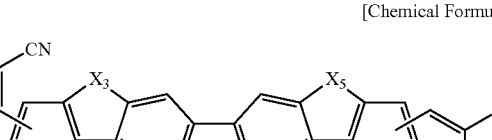

wherein, in Chemical Formulae 2 to 7,
each of $X_1$ to $X_5$ are one of the same and different and are independently one of $CR^1R^2$, $SiR^3R^4$, $NR^5$, oxygen (O), and selenium (Se), wherein each of $R^1$ to $R^5$ are independently one of hydrogen, a substituted or unsubstituted $C_1$ to $C_{10}$ alkyl group, a substituted or unsubstituted $C_6$ to $C_{20}$ aryl group, a substituted or unsubstituted $C_3$ to $C_{20}$ heteroaryl group, and a combination thereof.

14. The organic photoelectric device of claim 9, wherein the active layer selectively absorbs light of a green wavelength region.

15. The organic photoelectric device of claim 9, wherein the active layer shows a maximum absorption peak in a wavelength region of about 500 nm to about 600 nm.

16. The organic photoelectric device of claim 9, wherein the active layer has a band gap of about 2.0 eV to about 3.0 eV.

17. The organic photoelectric device of claim 9, wherein the first electrode is an anode and the second electrode is a cathode.

18. An image sensor comprising the organic photoelectric device of claim 9.

* * * * *